United States Patent [19]

Boltze

[11] Patent Number: 4,585,880

[45] Date of Patent: Apr. 29, 1986

[54] PROCESS FOR THE PREPARATION OF 1-(4-CHLOROBENZOYL)-5-METHOXY-2-METHYL-3-INDOLEACETOXYACETIC ACID

[75] Inventor: Karl-Heinz Boltze, Borod, Fed. Rep. of Germany

[73] Assignee: Troponwerke GmbH & Co. KG, Cologne, Fed. Rep. of Germany

[21] Appl. No.: 469,674

[22] Filed: Feb. 25, 1983

[30] Foreign Application Priority Data

Feb. 26, 1982 [DE] Fed. Rep. of Germany ....... 3206889

[51] Int. Cl.$^4$ ............................................ C07D 209/28
[52] U.S. Cl. .................................................... 548/501
[58] Field of Search ........................................ 548/501

[56] References Cited

U.S. PATENT DOCUMENTS 2,518,456  8/1950  Fein et al. ........................... 560/185
4,332,727  6/1982  Boltze et al. ......................... 548/501

FOREIGN PATENT DOCUMENTS 1131545  10/1968  United Kingdom ................ 548/501

OTHER PUBLICATIONS

Fisherova et al., Chem. Abst. 90:87267x (1979).

*Primary Examiner*—Glennon H. Hollrah
*Assistant Examiner*—D. B. Springer
*Attorney, Agent, or Firm*—Sprung Horn Kramer & Woods

[57] ABSTRACT

The invention relates to a process for the preparation of the known 1-(4-chlorobenzoyl)-5-methoxy-2-methyl-3-indoleacetoxyacetic acid which comprises reacting an indolecarboxylic acid of Formula (II) or its derivative with an alcohol of Formula (III). The final product is known to have antiinflammatory activity.

1 Claim, No Drawings

PROCESS FOR THE PREPARATION OF 1-(4-CHLOROBENZOYL)-5-METHOXY-2-METHYL-3-INDOLEACETOXYACETIC ACID

The present invention relates to a new process, which is chemically original and advantageous, for the preparation of the known 1-(4-chlorobenzoyl)-5-methoxy-2-methyl-3-indoleacetoxyacetic acid (designated I in the following text).

A number of processes have already been disclosed for the preparation of this known compound, compare, for example, DE-OS (German Published Specification) No. 2,234,651, DE-OS (German Published Specification) No. 2,257,867 and DE-OS (German Published Specification) No. 2,943,125. In the known processes, the carboxyl group is initially protected by a benzyl radical, so that catalytic hydrogenation of the benzyl ester in accordance with the reaction scheme below must be carried out in a final reaction step.

Reaction scheme:

During this removal of the benzyl radical, 1-benzoyl-5-methoxy-2-methyl-3-indoleacetoxyacetic acid, called the dechlorinated compound in the following text, is always produced as a by-product. This undesired impurity, which arises in an amount up to 0.5% by removal of the chlorine from the benzene ring of the 4-chlorobenzoyl radical, must subsequently be removed in elaborate purification steps, and this is associated with losses in yield.

The object of the present invention is to provide an alternative preparation process in which the undesired dechlorinated compound is not produced.

It has been found, surprisingly, that 1-(4-chlorobenzoyl)-5-methoxy-2-methyl-3-indoleacetoxyacetic acid I is obtained in a simple manner and in high purity when indolecarboxylic acid or its derivatives of the general formula II

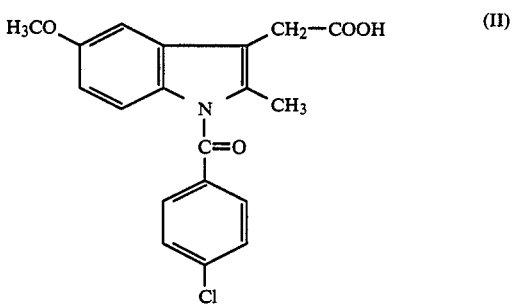

is reacted with compounds of the general formula III $$HO-CH_2-\overset{O}{\underset{\|}{C}}-O-R^2 \quad (III)$$

in which $R^2$ represents hydrogen or ammonium, in the presence of inert organic solvents, such as, for example, ethers, diethyl ether, diisopropyl ether, dioxane, tetrahydrofuran, 1,2-dimethoxyethane, chlorinated hydrocarbons, methylene chloride, chloroform, dichloroethane, substituted amides, dimethylformamide, N-methylpyrroliddone, aromatics, toluene, xylene, ketones, acetone, methyl ethyl ketone (2-butanone) in a temperature range from −10° C. to 80° C., preferably at −10° to 50° C., particularly preferably at −5° C. to 20° C.

If, as a representative of the general formula II, the hydroxylindolecarboxylic acid derivatives and compounds of the general formula III are used as starting materials, the course of the reaction can be represented by the following reaction scheme:

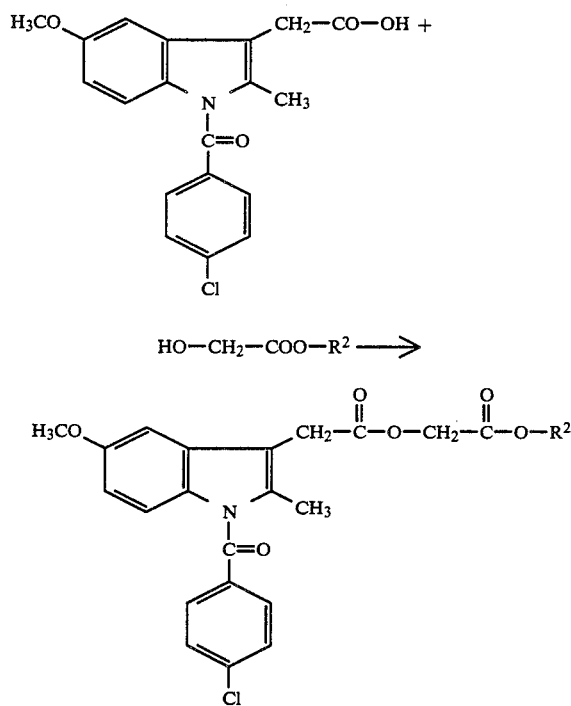

$R^2$ preferably represents an ammonium cation.

The ammonium compounds produced are subsequently converted into the final product I in a simple manner by treatment with acids.

It was surprising that 1-(4-chlorobenzoyl)-5-methoxy-2-methyl-3-indoleacetoxyacetic acid is produced by these processes in such a pure form, that is to say free of the interfering dechlorinated compound, and in yields of 60–70% of theory.

The compounds of the formula II and III used as starting materials are known or are prepared by known processes.

The final compound I prepared by the processes according to the invention is a valuable pharmaceutical active substance having an antiinflammatory effect, compare, for example, German Patent Specification No. 2,234,651.

In the direct esterification of the indolecarboxylic acid and glycolic acid (III, $R^2H$) carried out in the present process, 1-(4-chlorobenzoyl)-5-methoxy-2-methyl-3-indoleacetoxyacetic acid (I) is obtained by two routes (compare reaction schemes).

(a) Reaction scheme: Synthesis of I by direct esterification in the presence of $H^{\oplus}$:

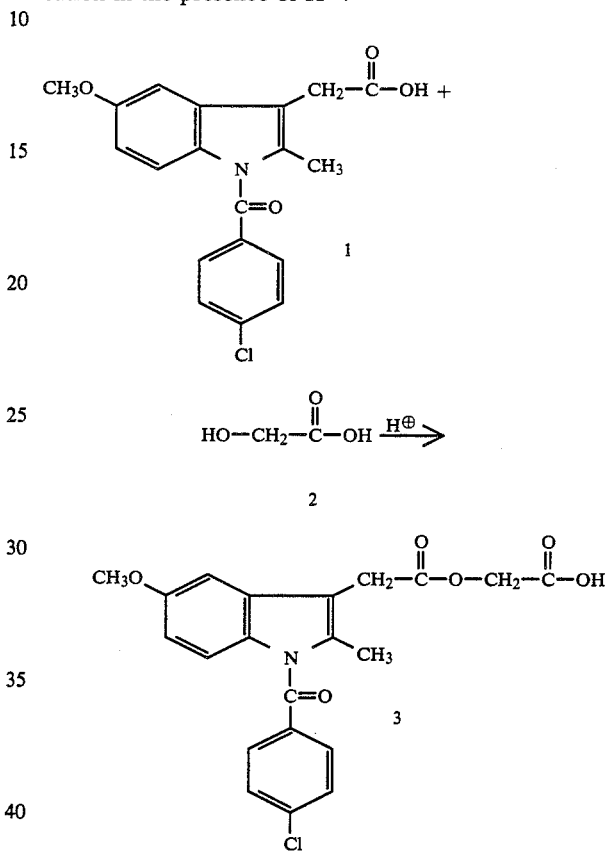

(b) Reaction scheme: Synthesis of I by direct esterification in the presence of DCC:

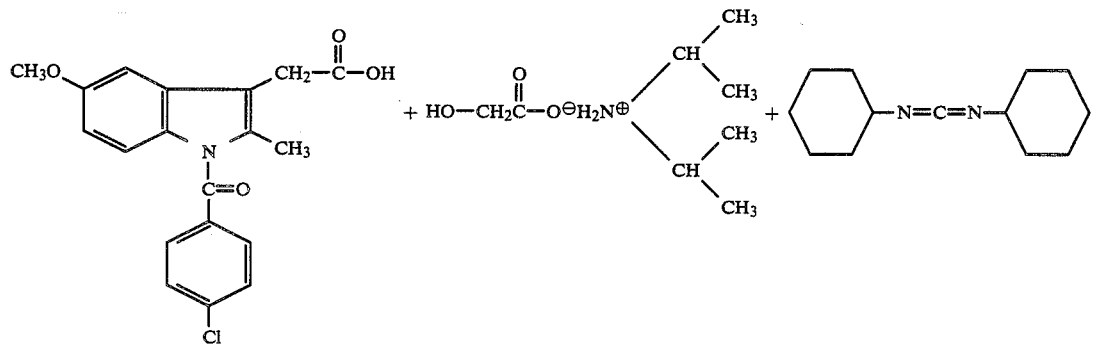

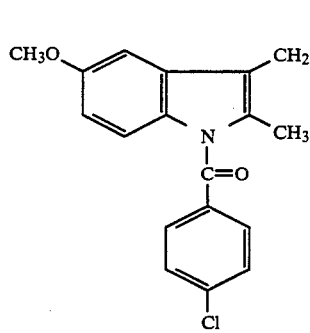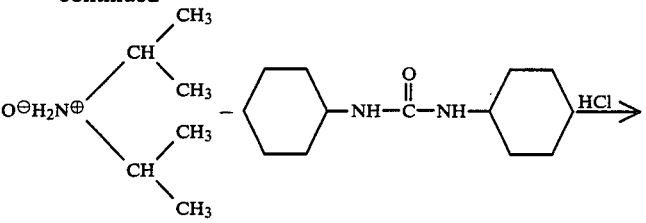

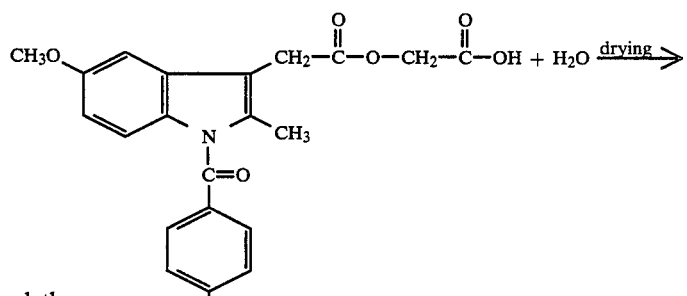

In one case, the indolecarboxylic acid (II) and the glycolic acid (III, R²H) are heated in an inert solvent, which is not miscible with water, preferably toluene, under a water separator for several hours. In this reaction, both the inherent proton activity of the glycolic acid and also that of a strong acid added, such as, for example, p-toluenesulphonic acid, can serve as the catalyst.

After chromatographic purification, I is obtained in a pure form. As an alternative to this, direct esterification is carried out by bringing the indolecarboxylic acid (II) to reaction with the diisopropylammonium glycolate, with exclusion of moisture, in the presence of a condensation agent, such as, for example, dicyclohexylcarbodiimide (DCC). The diisopropylammonium salt I is obtained as a colourless crystalline substance.

Chlorinated hydrocarbons, such as chloroform or methylene chloride are employed as the solvent, the latter being preferred. The reaction temperatures are between 0° and 50° C., preferably at 20° C.

The purified ammonium salt of I is converted into the free acid by addition of aqueous HCL and the colourless I monohydrate is crystallised carefully and completely. Ketones or ethers, which are miscible with water, are used as the solvent, preferably acetone or dioxane. The reaction temperatures are between 0° and 60° C., preferably 20° C. or 40° C.

The highly pure monohydrate loses its content of water in a gentle drying process and provides I as yellowish crystals, which melt at 151° to 152°.

EXAMPLE 1

(a) Direct esterification in the presence of H+ 3.6 g (0.01 mol) of II (R¹OH) and 3.8 g (0.05 mol) of glycolic acid are suspended in 40 ml of toluene and heated to boiling, with stirring, under a water separator for 64 hours. Water separation: 0.8 ml.

Toluene is distilled off, the residue is ground in a mortar and extracted with CH₂Cl₂.

The oily residue, which has been freed of solvent, is chromatographed on silica gel (mobile phase: cyclohexane/ethyl acetate/acetic acid: 10/10/1 v/v). Yield: 1.1 g of $^{Cl}$ 1-(4-chlorobenzoyl)-5-methoxy-2-methyl-3-indoleacetoxyacetic acid I=26.4% of theory.

(b) Direct esterification in the presence of DCC 10.8 g of II (R¹OH) and 7.1 g of diisopropylammonium glycolate (0.04 mol) are dissolved in 60 ml of CH₂Cl₂, with stirring and exclusion of moisture, at room temperature and then 6.2 g of dicyclohexylcarbodiimide (DCC) (0.03 mol) are added. Reaction is allowed to continue at room temperature for 3 hours and the precipitate produced is filtered off. The filtrate is freed of solvent in a rotary evaporator under a waterpump vacuum and 160 ml of ether are added to the syrupy residue. The solution is allowed to stand at room temperature over the weekend and the colourless crystalline ammonium salt of I is filtered off.

Conversion into I (free acid) is carried out by dissolving the ammonium salt thus obtained in 11 ml of acetone and 5 ml of H₂O with stirring. Then 8 ml of 1N HCl are added to this solution and it is seeded. The mixture is then stirred for 1 hour until crystallisation is complete. The colourless crystalline substance is filtered off with suction, thoroughly washed with H₂O and dried in a desiccator under a waterpump vacuum at 40° C. Yield: 3.35 g of 1-(4-chlorobenzoyl)-5-methoxy-2-methyl-3-indoleacetoxyacetic acid monohydrate=25.7% of theory.

On drying under a waterpump vacuum at 90° C. until removal of water is complete, I is obtained as yellowish crystals which melt at 151° to 152° C.

We claim:

1. A process for the production of 1-(4-chloro-benzoyl)methoxy-2-methyl-3-indoleacetoxyacetic acid which comprises reacting, in the presence of methylene chloride, 1-(4-chlorobenzoyl)-5-methoxy-2-methyl-3-indolacetic acid with diisopropylammonium glycolate, with the exclusion of moisture, and in the presence of dicyclohexylcarbodiimide, separating the diisopropylammonium salt from the reaction medium, then converting said diisopropylammonium salt to the free acid by acidification.

* * * * *